June 9, 1959 C. SKIMINA Plant Pat. 1,843
LANTANA PLANT
Filed July 14, 1958
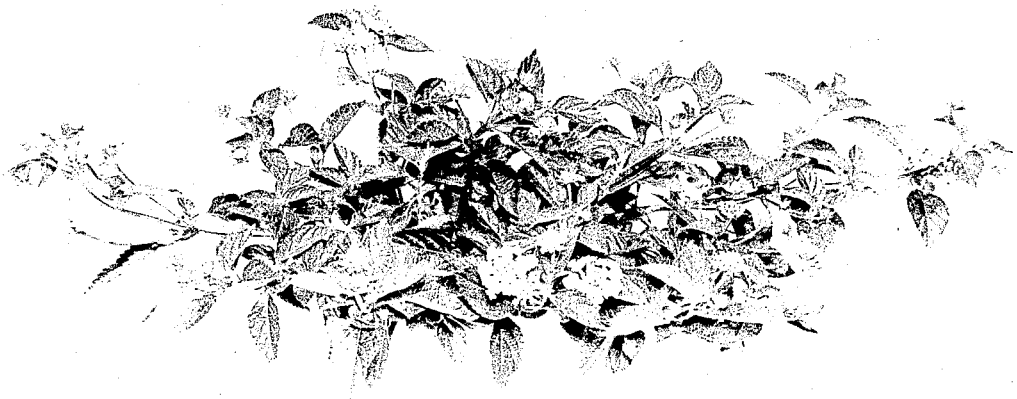
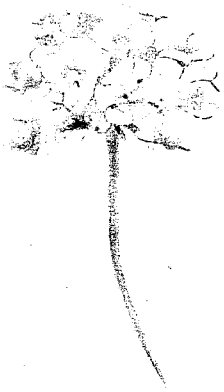
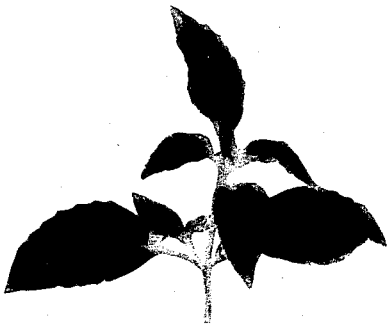
INVENTOR.
CONRAD SKIMINA
BY J. F. Cuneo
ATTORNEY United States Patent Office Plant Pat. 1,843
Patented June 9, 1959

1,843

LANTANA PLANT

Conrad Skimina, Azusa, Calif., assignor to Monrovia Nursery Co., Azusa, Calif., a corporation of California Application July 14, 1958, Serial No. 748,552

1 Claim. (Cl. 47—60)

The present invention relates to a new and distinct variety of plant belonging to the Lantana genus that is characterized as to novelty by its prostrate growing habit, abundance of large leaves and pink flowers. This plant has resulted from the cross breeding of *Lantana camara* Dwarf Pink, an unpatented variety, and *Lantana callowiana* Gold Rush, United States Plant Patent No. 1,211, after conducting numerous experiments in the Los Angeles area of southern California.

The cross breeding of the above identified species of Lantana has produced a new type as well as a new variety of Lantana that combines some of the characteristics and features of each of its parent plants. The new variety distinguishes from its parent plant *Lantana camara* Dwark Pink, in that the plant is prostrate in place of upright and the plant forms a densely foliated shrub having vine-like stems. The novel variety of Lantana differs from its parent *Lantana callowiana* Gold Rush in that the flowers are Rose Madder, the leaves are much larger and darker in color, and the plant is a more vigorous grower.

The blooms of the new variety consist of groups of individual florets arranged in substantially spherical umbels. The number of florets in each umbel varies slightly.

The accompanying illustrations include a black and white photographic representation showing the prostrate growth of the new variety of Lantana. The illustrations also include a full color reproduction of an individual umbel and also a full color reproduction of a typical leaf branch that brings out the shape, size and color of the leaves.

This novel variety of Lantana has been reproduced asexually by me in the Los Angeles area of southern California by means of cuttings. The distinguishing features and characteristics have been observed to be well established in all of the resulting plants. It has also been determined that the new species of Lantana cannot be reproduced by sexual means, the plant will not reproduce true from seed.

A detailed description of the new species of Lantana follows. All references to color names and numbers that appear in the description are taken from the standards shown in the Horticultural Colour Chart adopted by the British Colour Council.

*The plant*

Nature and growth: The plant is best described as being of the prostrate or trailing type. The plant forms a densely foliated shrub having many vine-like branches. This characteristic is clearly shown in the accompanying black and white photograph. The vine-like branches are approximately three feet in length and emanate from a central root structure.

Stems: The stems are slender and vine-like. Newly formed stems are at first succulent but as they become older attain a woody structure. When the stems have reached maturity they become stiff and are quite brittle.

Leaves: The foliage of the plant is persistent and is moderately dense, the leaves possess the following characteristics:

*Size.*—The average leaf is about one and one quarter inches wide and is generally about two and one quarter inches in length.

*Shape.*—The leaves are ovate and have serrated edges, the apex of the leaves is defined as acuminate. The base of the leaf is rounded.

*Arrangement.*—The arrangement of the leaves is opposite; the leaves are attached to the respective stem by a short peduncle.

*Color.*—The predominant color of the leaves is Spinach Green 0960.

*Appearance and texture.*—The leaves have a slightly creased, leathery appearance. The surface of the leaves are sparsely pubescent. The ribs are quite prominent on the under side of the leaves.

*Aroma.*—The leaves have a faint aroma that resembles slightly the odor of oil of eucalyptus and at the same time resembles the spicy odor of sage.

Blooming habit: The plant is a profuse bloomer.

*The flower*

Arrangement: The individual small flowers are clustered together and form a substantially hemispherical umbel that ranges in size from about one inch to one and one half inches in diameter. The number of florets in each umbel varies from twenty one to twenty three. The umbels are formed on strong axillary stems or peduncles that are from one and eleven sixteenths to one and three quarters inches in length. These flower peduncles show no pubescence. The flowers generally are formed on terminal growth.

Florets:

*Size.*—The individual florets are quite small ranging from five sixteenths to three eighths of an inch in width.

*Color.*—The color of the majority of the florets is Rose Madder No. 23/1. A few of the florets in the center are occasionally yellow.

*Aroma.*—The flowers have practically no aroma.

Having thus described my invention, I claim:

The new and distinct variety of Lantana plant substantially as herein shown and described, characterized especially by its abundance of of pink flowers and its combination of the prostrate, trailing growth habit of *Lantana callowiana* Gold Rush, with the Rose Madder coloration and larger and darker leaves of *Lantana camara* Dwarf Pink.

No references cited.